United States Patent [19]
Mierendorf et al.

[11] Patent Number: 5,856,144
[45] Date of Patent: Jan. 5, 1999

[54] DIRECT CLONING OF DNA FRAGMENTS

[75] Inventors: Robert C. Mierendorf, Madison; Robert E. Novy, Verona; Kristin M. Kolb, Madison, all of Wis.; David O'Reilly, Southampton, United Kingdom

[73] Assignee: Novagen, Inc., Madison, Wis.

[21] Appl. No.: 878,379

[22] Filed: Jun. 18, 1997

[51] Int. Cl.$^6$ ............ C12P 19/34; C12N 15/64; C12N 15/66; C12N 15/70

[52] U.S. Cl. .......... 435/91.2; 435/91.4; 435/172.1; 435/172.3; 435/320.1

[58] Field of Search .................. 435/91.2, 172.1, 435/91.4, 320.1, 172.3

[56] References Cited

U.S. PATENT DOCUMENTS 5,487,993  1/1996  Herrnstadt et al. ............... 435/172.3

OTHER PUBLICATIONS

Brownstein, Michael J., et al., "Modulation of Non–templated Nucleotide Addition by Taq DNA Polymerase: Primer Modifications that Facilitate Genotyping," *BioTechniques*, 20(6):1004–1010 (Jun. 1996).

Magnuson, V.L., et al., "Substrate Nucleotide–Determined Non–Templated Addition of Adenine by Taq DNA Polymerase: Implications for PCR–Based Genotyping and Cloning," *BioTechniques*, 21(4):700–709 (Oct. 1996).

Novy, Robert E., et al., "Perfectly Blunt Cloning: A superior method for cloning PCR products or any DNA," *InNovations*, 6:7–11 (Dec. 1996).

Testori et al. Direct Cloning of Unmodified PCR Products by Exploiting an Engineered Restriction Site. Gene. 143: 151–152, 1994.

Khan et al. A Simple Ligation Step Improves the Efficiency of T–Overhang Vectors. Trends In Genetics, 10(7): 225–226, Jul. 1994.

*Primary Examiner*—Nancy Degen
*Attorney, Agent, or Firm*—Quarles & Brady

[57] ABSTRACT

A vector for the direct cloning of the products of PCR protocol incorporates single nucleotide overhangs at one or both ends of a linearized DNA segment. The single nucleotide overhangs are uracil or inosine residues, as desired, to facilitate cloning of the desired PCR products.

12 Claims, No Drawings

DIRECT CLONING OF DNA FRAGMENTS

BACKGROUND OF THE INVENTION

There has been much technical development in recent years on methods for manipulating and copying DNA molecules for use in modern techniques of molecular biology and genetic engineering. A reaction known as the polymerase chain reaction, or PCR, described in U.S. Pat. Nos. 4,683,195 and 4,683,202, has become a standard laboratory method for reproducing, or amplifying, copies of a DNA molecule either from an in vitro product or from a native DNA sequence isolated from a living organism. A variety of methods have been developed for cloning the products of PCR amplification into a plasmid vector for the purposes of making large quantities of DNA analysis, or to express DNA as RNA or protein products by other in vitro and in vivo methods.

One common method for the cloning of the products of PCR reactions involves the use of circular plasmids which can be cut to produce DNA fragments with ends having single 3' dTMP overhangs. A single dAMP overhang present on the DNA insert can be conveniently ligated into a vector having complementary single dTMP overhangs. These so-called "T-vectors" are formed from two closely spaced sequences that are recognized by a specific restriction enzyme that cleaves the plasmid DNA to leave a single 3' dTMP overhang on each end of the linearized vector following cleavage. The use and construction of such a vector is described in U.S. Pat. No. 5,487,993. The T-vector is intended to take advantage of a phenomenon associated with some of the DNA polymerases that are used in the PCR process. For example, a popularly used DNA polymerase, Taq DNA polymerase, often leaves a single unpaired dAMP residue at each end of the DNA molecules which are the product of the PCR reaction. However, the propensity of Taq DNA polymerase to add single 3' dAMP extensions varies with the composition of the 3' ends of the PCR products, the PCR conditions, and the conditions under which the completed reactions are stored (Hu, *DNA Cell Biol.* 12, 763 (1993); Magnuson et al., *BioTechniques* 21, 700, (1996)). For example, the presence of a dAMP residue at the 3' end of a duplex is inhibitory to dAMP addition (presumably leaving a blunt end), and other bases such as dCMP, dGMP or dTMP can be preferentially added to ends having specific sequences. Therefore, under many conditions the fraction of PCR products that possess single 3' dAMP extensions on both ends can be relatively low. Therefore, vectors which have only a single 3' dTMP overhang cannot efficiently ligate with these other fragments. Also, while the theoretical cloning efficiency of a single T overhang and a single A overhang is high, practical cloning efficiencies are sometimes lower, and there can be high numbers of false positives arising from vector religation, due to damage of the DNA ends caused by exonuclease contamination of the restriction enzyme, or religation of the small vector fragment produced by restriction enzyme cleavage instead of the PCR product.

There are other methods for preparing T vectors including the addition of single dideoxy TMP residues at each end of a blunt and linearized plasmid using terminal transferase Holton & Graham, *Nucleic Acids Res.* 19:1156 (1991), or the addition of linkers containing a single unpaired dTMP residue to a linearized plasmid. However, no method has been described for the preparation of vectors having bases other than dTMP as the single 3' overhang.

Technology generally desires cloning vectors which optimize or improve efficiency over other vectors then currently available.

BRIEF SUMMARY OF THE INVENTION

The present invention is summarized in that a vector for use in the direct cloning of DNA fragments contains at at least one end thereof an overhang of a single nucleotide, the nucleotide being a nucleotide which does not normally occur in DNA, such as a uracil or an inosine residue. The resulting single overhang vector can conveniently be used for the direct cloning of the products of PCR reactions in a convenient and useful manner.

It is another object of the present invention to describe a method for cloning the direct products of PCR reaction using linearized vectors having a single overhang of non-natively occurring nucleotides, including uracil and inosine.

It is another object of the present invention to allow the construction of vectors having one or two single nucleotide overhangs in order to selectively clone particular PCR products.

It is a feature of the present invention that the cloning vectors created with single overhangs, including non-naturally occurring DNA nucleotides, have the inherent characteristic of binding to a wider range of PCR reaction products single nucleotide overhangs than previously available vectors having only a single T overhang.

Other objects, advantages and features of the present invention will become apparent from the following specification.

DETAILED DESCRIPTION OF THE INVENTION

In accordance with the present invention a cloning vector is described in which there is a single nucleotide overhang at the 3' end of each end of the vector. The single nucleotide overhang is of a nucleotide which does not occur normally in DNA, the preferable nucleotides being uracil (U) and inosine (I). Uracil and inosine are both naturally occurring nucleotides, uracil being incorporated in both mRNA and tRNA and inosine also being present in tRNA. Uracil forms hydrogen bonds with adenine (A) while inosine preferentially binds to cytosine (C). This cloning plasmid can be readily used for the direct cloning of the products of polymerase chain reaction (PCR) protocols which normally contain a complementary single nucleotide overhang on those products. The vectors described in this patent application are intended to be an extension of, and an improvement upon, the vectors having a single T overhang as described in U.S. Pat. No. 5,487,993, the specification of which is hereby incorporated by reference.

The vectors of the present invention extend the capability of in vitro methods of cloning PCR reaction products, and vector preparation, to incorporate nucleotide residues that do not naturally occur in native DNA. These vectors improve the cloning of DNA fragments tailed with single dAMP overhangs. The use of dUMP in place of dTMP as the single end overhang at each end of the vector allows for the potential of more efficient cloning of dTMP-containing inserts since at least for RNA to DNA interactions, the hydrogen bond formed between the nucleotides A and U is stronger than that between the nucleotides T and A. More importantly the use of single nucleotide overhanging additions other than dTMP, such as dIMP, provides the ability to clone fragments containing extensions other than dAMP on the reaction products of the PCR protocol. dIMP can in theory base pair with multiple residues, but practical experience to date suggests dIMP has a practical preference for annealing with dCMP. Virtually any nucleotide that can be synthesized and incorporated into a DNA chain can serve as the 3' extended base allowing for improvements in cloning efficiency and versatility as other nucleotide modifications are developed. It thus becomes possible to clone a variety of species found in a PCR reaction product mix with greater efficiency and selectability than it was heretofore possible.

In general, the cloning vectors of the present invention will be created by making a blunt ended cloning vector and then adding to each end of the blunt end a single 3' nucleotide overhang. Circular DNA vectors are commonly blunt-ended by digestion with restriction enzymes which have a cutting site leaving a blunt end, such as EcoRV or SmaI. The blunt ended vector can be incubated in a reaction mixture with only the nucleotide sought to be added (e.g., dUTP or dITP), in the presence of an enzyme, such as Taq or Tth DNA polymerases, each of which will add a single nucleotide overhang to a blunt ended double stranded DNA segment.

An alternative strategy for the products of some PCR reactions is to construct a vector having one blunt end and a single U or I overhang at the other end. A vector of this variation is particularly useful for cloning of PCR products which have a single A overhang only at one of their ends. Since the addition of the dAMP overhang to a PCR product by Taq DNA polymerase, for instance, is dependent to some degree on the DNA sequence of the PCR product, it is not uncommon for a significant fraction of such products to have an overhang only at one end. To make such a single end single overhang vector, one could begin with a vector which is linearized with a restriction enzyme, such as ECORV, which produces blunt ends. Then the single uracil or inosine residue can be added to both ends of the linear vector. Following that, digestion with another blunt-ending endonuclease, such as SmaI, could cleave the vector closely adjacent to only one end to leave one blunt end and one single overhand end. This variation has the advantage of directionality, i.e., the PCR product will ligate into the vector in only one orientation. For this reason, it may be desirable to design PCR primers so as to encourage the production of PCR products which have a single A overhang only at one end, while the other end is blunt. This can be conveniently done by designing the PCR primers so that one primer includes a sequence which discourages the addition of a dAMP (e.g. 5'-TCAGGG . . . ) while the other primer includes a sequence favoring dAMP addition (e.g. 5'-GTTTCTT . . . ). Thus direct directional cloning of PCR products becomes practical.

The cloning vector constructed in accordance with the present invention may also have any of the many other components commonly carried on cloning and expression vectors. Such components may include a selectible marker such as for antibiotic resistance. The vector should also have an origin of replication to permit high copy number replication in commonly used host cells. Such cloning vectors also usually include a plurality of restriction sites forming a polylinker or multiple cloning site, located adjacent to each side of the single nucleotide overhang to allow easy subcloning of the fragments into other vectors or for the addition of promoters for expression. The vector may also include a bacteriophage origin of replication to allow production of single stranded copies of the recombinant vector for use in, among other things, sequencing procedures. The vector may also include a gene spanning the cloning site which creates an easily detectible phenotype to allow for selection of inserts, such as for example the LacZα gene which is used to span a cloning site to allow for convenient blue-white color screening for recombinant vectors which include an insert at the site within the LacZα gene. Another feature which can be included in such a vector is a positive selection sequence which permits survival of recombinants which disrupt a lethal gene.

The vector in accordance with the present invention can be sold separately or as part of a cloning kit. The vector would typically be a linearized piece of DNA with the single U or I nucleotide overhang at each 3' end thereof. The vector can be sold with competent host cells with a suitable genotype and which are competent for transformation. The vector may also be sold with an aliquot of a DNA ligase enzyme and buffers which may be conveniently used to ligate PCR amplification products into the vector. A kit including the vector might also include nuclease free water or control inserts with mononucleotide overhangs to check procedures for using the vector. Lastly, the kit may also include a supercoiled plasmid used as a transformation control.

EXAMPLE

A Comparison of U and I-Vectors with T-Vectors

To test the utility of the invention for cloning DNA fragments, vectors were prepared which contained either single 3' dUMP (U-Vector) or dIMP (I-Vector) residues. These vectors were tested by ligating synthetic DNA molecules containing eac of the four naturally occurring nucleotides as single 3' extensions (i.e. dAMP, dTMP, dCMP or dGMP) and transforming the ligation mixtures into competent *E. coli* cells. The resulting colonies were screened for the presence of inserts.

1. Method of U-Vector and I-Vector Preparation

Both the U and I-Vectors were prepared from pT7Blue (Novagen) using the procedures contained in the manufacturer's documentation, using a modification of the Taq DNA polymerase method described by Marchuk et al. (*Nucleic Acids Res.* 19, 1154 (1991)) for T-vectors.

2. I-Vector, U-Vector Versus T-Vector Comparison

A current lot of Novagen's pT7Blue T-Vector was compared with the U and I-Vectors. The vectors were ligated in separate reactions to four synthetic 50 base pair inserts (annealed HPLC purified oligos) which possessed either single 3'-A, 3'-T, 3'-G or 3'-C overhangs respectively at each end. A 212 bp PCR product containing single 3' A overhangs was also tested for cloning in the case of the U-vector. The ligation reaction was transformed into NovaBlue competent cells (Novagen) and the resulting colonies screened by the blue/white method on X-gal/IPTG plates as described in Novagen's published T-Vector protocol. Note that 5 μl of the final transformation reaction were plated for the 50 bp inserts and 10 μl plated for the 212 bp PCR insert. Selected blue or white colonies were then subjected to colony PCR analysis (Gussow & Clackson. *Nucleic Acids Res.* 17, 4000 (1989)) and/or sequenced to detect the presence of inserts. The results are summarized below.

| Vector | Insert | # White cfu | # Blue cfu | Colony PCR # positives/ # tested | # and Type Sequenced |
|---|---|---|---|---|---|
| T-Vector | 50 bp 3'-A | >2,000 | 3 | 20/20 | |
| | 50 bp 3'-T | 7 | 2 | Not done | |
| | 50 bp 3'-G | 6 | 3 | Not done | |
| | 50 bp 3'-C | 5 | 4 | Not done | |
| | No insert | 5 | 10 | Not done | |

-continued

| Vector | Insert | # White cfu | # Blue cfu | Colony PCR # positives/ # tested | # and Type Sequenced |
|---|---|---|---|---|---|
| U-Vector | 50 bp 3'-A | 1,818 | 142 | 20/20 | 6 white |
|  | 50 bp 3'-T | 3 | 111 | Not done |  |
|  | 50 bp 3'-G | 6 | 109 | Not done |  |
|  | 50 pb 3'-C | 7 | 152 | Not done |  |
|  | No insert | 5 | 110 | Not done |  |
|  | 212 bp PCR | 229 | 225 | 14/18 |  |
| I-Vector | 50 bp 3'-A | 6 | 2 | Not done | 2 white/2 blue |
|  | 50 bp 3'-T | 7 | 6 | Not done |  |
|  | 50 bp 3'-G | 7 | 2 | Not done |  |
|  | 50 bp 3'-C | 448 | 410* | 10/10 white phenotype 10/10 blue phenotype |  |
|  | No insert | 6 | 3 | Not done |  |

*Note:
The vast majority of cfu scored as blue are believed to contain the 50 bp insert (since background was so low in all other cases) and exhibit a blue phenotype due to translation reinitiation or frameshifting. To verify that the blue cfu contained inserts 2 white and 2 blue cfu were subjected to cycle sequencing with the Cy5-T7 promoter primer. As expected all colonies contained inserts, the insert was present in one orientation in the white cfu and present in the opposite orientation in the blue cfu. At every I-vector: 3'-C 50 bp insert junction dIMP was replaced by dGMP after replication in bacteria. Therefore, the I-vector: 3'-C insert junction differs from both the T and U-vector: insert junctions.

In conclusion, this experiment has shown that (1) a U-vector performed essentially equivalently to a T-vector for cloning synthetic fragments having dAMP extensions and that the U-vector could clone a PCR product, (2) an I-vector was capable of cloning fragments having dCMP extensions, whereas these fragments were not cloned using either T-vectors or U-vectors, and (3) synthetic fragments containing dTMP or dGMP extensions were not cloned by any of the vectors tested under these conditions. However, these synthetic fragments can be cloned using A-vectors and C-vectors respectively. The results demonstrate the principle of using alternative bases for preparing vectors that are able to accept inserts having extensions other than dAMP.

We claim:

1. A DNA vector comprising a linearized double stranded DNA molecule with a single unpaired nucleotide overhang at at least one 3' end thereof, the single overhanging nucleotide being selected from the group consisting of a uracil residue and an inosine residue.

2. A vector as claimed in claim 1 wherein the single overhanging nucleotide is a uracil residue.

3. A vector as claimed in claim 1 wherein the single overhanging nucleotide is an inosine residue.

4. A vector as claimed in claim 1 wherein there is a single overhanging nucleotide at each end of the DNA molecule.

5. A kit for the direct cloning of PCR products comprising
an aliquot of a DNA vector comprising a linearized double stranded DNA molecule with a single unpaired nucleotide overhang at each 3' end thereof, the single overhanging nucleotide being selected from the group consisting of a uracil residue and an inosine residue; and
an aliquot of a DNA ligase which catalyzes ligation between the DNA vector and PCR products.

6. A kit as claimed in claim 5 wherein there is a single overhanging nucleotide at each end of the DNA vector.

7. A kit for the direct cloning of PCR products comprising
an aliquot of a DNA vector comprising a linearized double stranded DNA molecule with a single unpaired nucleotide overhang at at least one 3' end thereof, the single overhanging nucleotide being selected from the group consisting of a uracil residue and an inosine residue; and
an aliquot of competent cells which hosts the vector for replication once a PCR product has been ligated into the vector.

8. A kit as claimed in claim 7 wherein there is a single overhanging nucleotide at each end of the DNA vector.

9. A method of direct cloning of PCR products for a target DNA sequence comprising the steps of
performing a polymerase chain reaction procedure to amplify copies of a target DNA sequence producing a plurality of PCR products with single nucleotide overhangs at each end thereof;
forming a ligation mixture including the PCR products and a linear DNA vector having a single unpaired nucleotide overhang at at least one 3' end thereof, the single overhanging nucleotide being selected from the group consisting of a uracil residue and an inosine residue, the ligation mixture being under conditions favoring ligation of the PCR products not the DNA vector; and
transforming the ligated vector into a competent host.

10. The method of claim 9 wherein the single nucleotide overhang is a uracil nucleotide.

11. The method of claim 9 wherein the single nucleotide overhang is an inosine nucleotide.

12. The method of claim 9 wherein there is a single nucleotide overhanging at each end of the DNA vector.

* * * * *